(12) United States Patent
Okamoto

(10) Patent No.: US 8,357,625 B2
(45) Date of Patent: Jan. 22, 2013

(54) CATALYST AND METHOD FOR PRODUCING CARBOXYLIC ACID AND/OR CARBOXYLIC ANHYDRIDE IN THE PRESENCE OF THE CATALYST

(75) Inventor: Atsushi Okamoto, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 560 days.

(21) Appl. No.: 12/487,158

(22) Filed: Jun. 18, 2009

(65) Prior Publication Data

US 2010/0036138 A1 Feb. 11, 2010

(30) Foreign Application Priority Data

Jun. 19, 2008 (JP) ................. 2008-160410

(51) Int. Cl.

| | |
|---|---|
| *B01J 21/18* | (2006.01) |
| *B01J 23/00* | (2006.01) |
| *B01J 23/40* | (2006.01) |
| *B01J 23/74* | (2006.01) |
| *B01J 21/02* | (2006.01) |
| *B01J 27/00* | (2006.01) |
| *B01J 27/198* | (2006.01) |
| *B01J 27/188* | (2006.01) |
| *B01J 27/19* | (2006.01) |
| *B01J 27/185* | (2006.01) |
| *B01J 27/182* | (2006.01) |
| *B01J 27/057* | (2006.01) |
| *B01J 21/00* | (2006.01) |
| *B01J 23/02* | (2006.01) |
| *B01J 23/20* | (2006.01) |
| *B01J 23/08* | (2006.01) |
| *B01J 3/06* | (2006.01) |
| *B01J 3/08* | (2006.01) |
| *C01B 31/06* | (2006.01) |
| *C04B 35/52* | (2006.01) |
| *C04B 35/48* | (2006.01) |
| *C04B 35/49* | (2006.01) |
| *B24D 3/02* | (2006.01) |
| *C09C 1/68* | (2006.01) |
| *C09K 3/14* | (2006.01) |

(52) U.S. Cl. ........ 502/182; 502/184; 502/185; 502/202; 502/208; 502/209; 502/210; 502/211; 502/213; 502/214; 502/215; 502/240; 502/242; 502/243; 502/246; 502/247; 502/248; 502/249; 502/254; 502/255; 502/256; 502/309; 502/310; 502/311; 502/312; 502/317; 502/319; 502/320; 502/321; 502/323; 502/344; 502/351; 502/352; 502/353; 502/354; 502/355; 423/446; 501/99; 501/100; 501/103; 51/309

(58) Field of Classification Search .................. 502/182, 502/184, 185, 202, 208–211, 213–215, 240, 502/242, 243, 246–249, 254–256, 309–312, 502/317, 319–323, 344, 351–355; 423/446; 501/99, 100, 103; 51/309
See application file for complete search history.

(56) References Cited

U.S. PATENT DOCUMENTS 3,064,084 A 11/1962 Meacham
(Continued)

FOREIGN PATENT DOCUMENTS

DE 1 141 343 12/1962
(Continued)

OTHER PUBLICATIONS

Kogyo Kagaku Zassi, vol. 55, No. 2, 1952, pp. 68-71.
(Continued)

*Primary Examiner* — Patricia L Hailey
(74) *Attorney, Agent, or Firm* — Oblon, Spivak, McClelland, Maier & Neustadt, L.L.P.

(57) ABSTRACT

An object of the present invention is to provide a catalyst exhibiting excellent performance particularly in partial oxidation reaction. Another object is to provide a method for efficiently producing carboxylic acid or carboxylic anhydride through vapor-phase partial oxidation of an organic compound by use of an oxygen-containing gas in the presence of the catalyst. The catalyst contains (1) diamond; (2) at least one species selected from among Group 5 transition element oxides, collectively called oxide A; and (3) at least one species selected from among Group 4 transition element oxides, collectively called oxide B. The method for producing a carboxylic acid or a carboxylic anhydride includes subjecting an organic compound to vapor phase partial oxidation by use of an oxygen-containing gas in the presence of the catalyst, wherein the organic compound is an aromatic compound having one or more substituents in a molecule thereof, the substituents each including a carbon atom bonded to an aromatic ring.

18 Claims, 2 Drawing Sheets

U.S. PATENT DOCUMENTS

| | | | |
|---|---|---|---|
| 4,100,106 A | | 7/1978 | Stefani et al. |
| 4,356,112 A | | 10/1982 | Nakanishi et al. |
| 4,397,768 A | * | 8/1983 | Felice ............................ 502/159 |
| 4,665,200 A | | 5/1987 | Nakanishi et al. |
| 5,252,752 A | * | 10/1993 | Aono et al. .................... 549/249 |
| 5,792,719 A | | 8/1998 | Eberle et al. |
| 6,099,819 A | * | 8/2000 | Srinivas et al. ............ 423/573.1 |
| 6,153,767 A | | 11/2000 | Sagane et al. |
| 6,452,021 B1 | | 9/2002 | Takahashi et al. |
| 6,660,681 B1 | | 12/2003 | Ledoux et al. |
| 2007/0031694 A1 | | 2/2007 | Hosonuma et al. |
| 2010/0314295 A1 | * | 12/2010 | Sandstede et al. ............ 208/143 |
| 2012/0015284 A1 | * | 1/2012 | Merzougui et al. ............ 429/520 |

FOREIGN PATENT DOCUMENTS

| | | | |
|---|---|---|---|
| DE | 2 040 455 | | 2/1972 |
| JP | 45-15018 | | 5/1970 |
| JP | 45-015018 | * | 5/1970 |
| JP | 48-22594 | | 7/1973 |
| JP | 49-041036 | * | 11/1974 |
| JP | 49-41036 | | 11/1974 |
| JP | 51-95990 | | 8/1976 |
| JP | 57-105241 | | 6/1982 |
| JP | 59-1378 | | 1/1984 |
| JP | 61-28456 | | 2/1986 |
| JP | 2005-255181 | | 10/1993 |
| JP | 7-2864 | | 1/1995 |
| JP | 7-171393 | | 7/1995 |
| JP | 8-318160 | | 12/1996 |
| JP | 2000-1484 | | 1/2000 |
| JP | 2002-105078 | | 4/2002 |
| JP | 2002-105079 | | 4/2002 |
| WO | WO 00/62926 | | 10/2000 |
| WO | 2010/143690 | * | 12/2010 |

OTHER PUBLICATIONS

Nippon Kagaku Zassi, vol. 82, No. 3, 1961, pp. 276-285.
Catalyst, vol. 8, 1966, pp. 302-307.
Khushrav E. Nariman, et al., "Design, Synthesis, and Properties of Chemical Vapor Deposited Diamond on Inorganic Oxide Catalysts: Experimentation and Simulation", Ind. Eng. Chem. Res., vol. 32, No. 2, 1993 pp. 263-273.
Extended European Search Report issued on Jun. 1, 2011 in corresponding European Application No. 09 16 2948.
Kiyoharu Nakagawa et al., "Novel Selective Oxidation of Light Alkanes Using Carbon Dioxide. Oxidized Diamond as a Novel Catalytic Medium", Chemistry Letters, vol. 32, No. 9, 2003, pp. 866-867.

* cited by examiner

CATALYST AND METHOD FOR PRODUCING CARBOXYLIC ACID AND/OR CARBOXYLIC ANHYDRIDE IN THE PRESENCE OF THE CATALYST

BACKGROUND OF THE INVENTION

1. Field of the Invention

The present invention relates to a catalyst and to a method for producing a carboxylic acid and/or a carboxylic anhydride through vapor-phase partial oxidation of an organic compound in the presence of the catalyst by use of an oxygen-containing gas.

2. Background Art

There has been already known method for producing carboxylic acids through vapor-phase partial oxidation of an organic compound in the presence of a catalyst containing diamond and a Group 5 transition element oxide. Ind. Eng. Chem. Res., 32, 263-273 (1993) discloses a method for growing a porous diamond layer on a metal oxide surface through chemical vapor deposition. The non-patent document describes that the selectivity of the catalytic reaction to form phthalic anhydride through vapor-phase partial oxidation of o-xylene is estimated to be enhanced to a certain extent, based on the simulation results using a specific mathematical model and specific parameters, assuming that a diamond layer can be grown in a vanadium pentoxide ($V_2O_5$) surface without impairing its oxidation catalytic activity. The document also discloses that CVD growth of the diamond layer is performed under high-temperature/low-pressure conditions (400 to 500° C. and 25 Torr) in a methane-hydrogen mixture (reducing gas) atmosphere. Meanwhile, under such conditions, vanadium pentoxide is known to be rapidly reduced to low-valence vanadium oxides (see Kogyo Kagaku Zassi, 55, p. 68 (1952), and Nippon Kagaku Zassi 82, p. 276 (1961)), and is known to exhibit insufficient oxidation catalytic activity (see Catalyst, 8, p. 302 (1966)). In other words, in practice, CVD growth disclosed in the aforementioned non-patent document encounters difficulty in producing a vanadium pentoxide catalyst bearing a diamond layer and having a sufficient oxidation catalytic activity. In addition, CVD must be performed by means of a particular processing apparatus with low process efficiency, making CVD a catalyst production method of limited effectiveness. Ind. Eng. Chem. Res., 32, 263-273 (1993) does not address addition of a transition metal element oxide other than vanadium oxide, addition method of a diamond other than CVD, or the morphology of a diamond other than layered structure by CVD growth.

There have already known a large number of methods for producing carboxylic acids through vapor-phase partial oxidation of an organic compound by use of an oxygen-containing gas in the presence of a catalyst containing a Group 5 transition element oxide (particularly vanadium pentoxide), a Group 4 transition element oxide, and a Group 6 transition element oxide. Examples of vapor-phase partial oxidation of a lower hydrocarbon compound or a lower oxygen-containing organic compound include production of acetic acid from butene in the presence of a catalyst such as $MoO_3$—$WO_3$—$V_2O_5$ catalyst (see German Patent No. 2,040,455); production of maleic anhydride from a linear C4 compound such as n-butane in the presence of a catalyst such as $V_2O_5$—$P_2O_5$—$TiO_2$ catalyst (see Japanese Patent 1976-95990A); and production of maleic anhydride from benzene in the presence of a catalyst such as $V_2O_5$—$WO_3$—$P_2O_5$—$TiO_2$ catalyst (see German Patent No. 1,141,343).

There has already been known vapor-phase partial oxidation of an aromatic compound having a substituent by use of an oxygen-containing gas. Specific examples include production of benzoic acid from toluene in the presence of a catalyst such as $V_2O_5$—$TiO_2$—$TeO_2$—$Sb_2O_3$ catalyst (see Japanese Patent 1993-255181A); production of phthalic anhydride from o-xylene in the presence of a catalyst such as $V_2O_5$—$TiO_2$—$Nb_2O_5$—$P_2O_5$—$K_2O$ catalyst (see Japanese Patent 1974-41036B); production of phthalic anhydride from naphthalene in the presence of a catalyst such as $V_2O_5$—$Nb_2O_5$—$TiO_2$—$P_2O_5$ catalyst (see Japanese Patent 1984-1378B); production of pyromellitic dianhydride from 1,2,4,5-tetraalkylbenzene including durene in the presence of a catalyst such as $V_2O_5$—$TiO_2$—$MoO_3$—$P_2O_5$ catalyst (see Japanese Patent 1970-15018B), $V_2O_5$—$TiO_2$—$Ag_2O$—$MoO_3$—$P_2O_5$—$CaO$ catalyst (see Japanese Patent 1995-171393A), or a layered catalyst of $V_2O_5$—$MoO_3$—$P_2O_5$—$Ag_2O$ and $V_2O_5$—$TiO_2$-rare earth metal oxide-$P_2O_5$—$CeO_2$ (see Japanese Patent 2000-1484A) and production of pyromellitic dianhydride from 2,4,5-trialkylbenzaldehyde in the presence of a catalyst such as $V_2O_5$—$TiO_2$—$P_2O_5$—($Sb_2O_5$, $Cs_2O$) catalyst (see Japanese Patent 1995-2864A) or $V_2O_5$—$TiO_2$—$Ag_2O$—$MoO_3$—$P_2O_5$ catalyst (see Japanese Patent 2002-105078A and 2002-105079A).

As described above, the aforementioned patent documents disclose use of a catalyst containing a Group 5 transition element oxide (particularly vanadium pentoxide) with a Group 4 transition element oxide and/or a Group 6 transition element oxide in the production of carboxylic acids through vapor-phase partial oxidation of an organic compound by use of an oxygen-containing gas. However, these patent documents do not mention a similar catalyst containing diamond.

Those catalysts disclosed in the patent documents improve catalytic activity, reaction selectivity, and stability in performance to satisfactory technical levels. However, there is still demand for a more effective catalyst. In particular, in partial oxidation, high reaction selectivity is demanded. In order to improve the selectivity, investigations have generally been performed on additives to the catalyst. Thus, catalysts attaining high selectivity generally contain a large number of components. Such catalysts raise problems in that preparation thereof including blending a number of starting materials and preliminary treatments, is cumbersome, and that the ranges of catalyst composition and reaction conditions for attaining optimum reaction results are limited. In order to solve the problems, it would be advantageous to find catalyst additives which are readily usable and are adaptable to wide ranges of catalyst preparation conditions and reaction conditions.

Meanwhile, vapor-phase partial oxidation of an organic compound by use of an oxygen-containing gas is known to be a vigorously exothermic reaction involving complete combustion. Therefore, there have been widely employed an approach that a catalyst composition containing a Group 5 transition element oxide is caused to be supported on a carrier which is inert to the relevant reaction, to thereby disperse heat. In fact, Japanese Patent 1982-105241A and 1986-28456A disclose self-sintered shaped carriers made of high-purity silicon carbide serving as suitable carriers. However, since such carriers are produced in an inert (non-oxidizing) gas (e.g., nitrogen) atmosphere via a sintering step at very high temperature, the production cost problematically increases. Among silicon carbide carriers, those having a low-purity and containing silica are inexpensive and can be produced in a simple manner through calcinating in air at low temperature. However, such a silicon carbide carrier encounters difficulty in exhibiting good reaction results. Therefore, finding catalyst additives which enable use of inexpensive carriers would be of great industrial value.

Apart from the development of the aforementioned catalyst carriers, development of catalyst itself; i.e., an approach in which a substance which disperse heat is added to a catalyst composition containing a Group 5 transition element oxide has been studied. For example, Japanese Patent 1996-318160A, U.S. Pat. No. 6,660,681, and WO 2000/62926 (pamphlet) disclose such additives; granular silicon carbide;

silicon nitride, boron nitride, and aluminum nitride; and granular β-silicon carbide, respectively. However, these patent documents do not disclose a catalyst composition or a catalyst containing diamond.

SUMMARY OF THE INVENTION

In view of the foregoing, an object of the present invention to solve the aforementioned problems involved in conventional techniques is to provide a catalyst exhibiting excellent performance particularly in partial oxidation reaction. Another object is to provide a method for efficiently producing carboxylic acid or carboxylic anhydride through vapor-phase partial oxidation of an organic compound by use of an oxygen-containing gas in the presence of the catalyst.

The present inventors have carried out extensive studies on vapor-phase partial oxidation of an organic compound by use of an oxygen-containing gas in the presence of a solid catalyst, and have found that the objects can be attained by use in effective combination of diamond, a Group 5 transition element oxide, and a Group 4 metal oxide, whereby the organic compound can be vapor-phase partial-oxidized effectively by use of an oxygen-containing gas, to thereby produce carboxylic acid or carboxylic anhydride. The present invention has been accomplished on the basis of this finding.

Accordingly, in a first aspect of the present invention, there is provided a catalyst comprising:
(1) diamond;
(2) at least one species selected from among Group 5 transition element oxides, collectively called oxide A; and
(3) at least one species selected from among Group 4 transition element oxides, collectively called oxide B.

The catalyst may further contain (4) at least one species selected from among Group 6 transition element oxides, collectively called oxide C.

The catalyst may further contain (5) at least one species selected from among oxides of the typical elements of Groups 1, 13, 14, 15, and 16, excepting a carbon element, collectively called oxide D.

In a second aspect of the present invention, there is provided a catalyst-on-carrier comprising a carrier and the aforementioned catalyst supported by the carrier.

In a third aspect of the present invention, there is provided a method for producing a carboxylic acid or a carboxylic anhydride comprising subjecting an organic compound to vapor phase partial oxidation by use of an oxygen-containing gas in the presence of the catalyst or catalyst-on-carrier as described above, wherein the organic compound is an aromatic compound having one or more substituents in a molecule thereof, the substituents each including a carbon atom bonded to an aromatic ring.

According to the present invention, there can be provided a catalyst exhibiting excellent performance particularly in partial oxidation reaction, and a method for efficiently producing carboxylic acid or carboxylic anhydride through vapor-phase partial oxidation of an organic compound by use of an oxygen-containing gas in the presence of the catalyst.

DETAILED DESCRIPTION OF PREFERRED EMBODIMENTS

Catalysts

Figure 1:
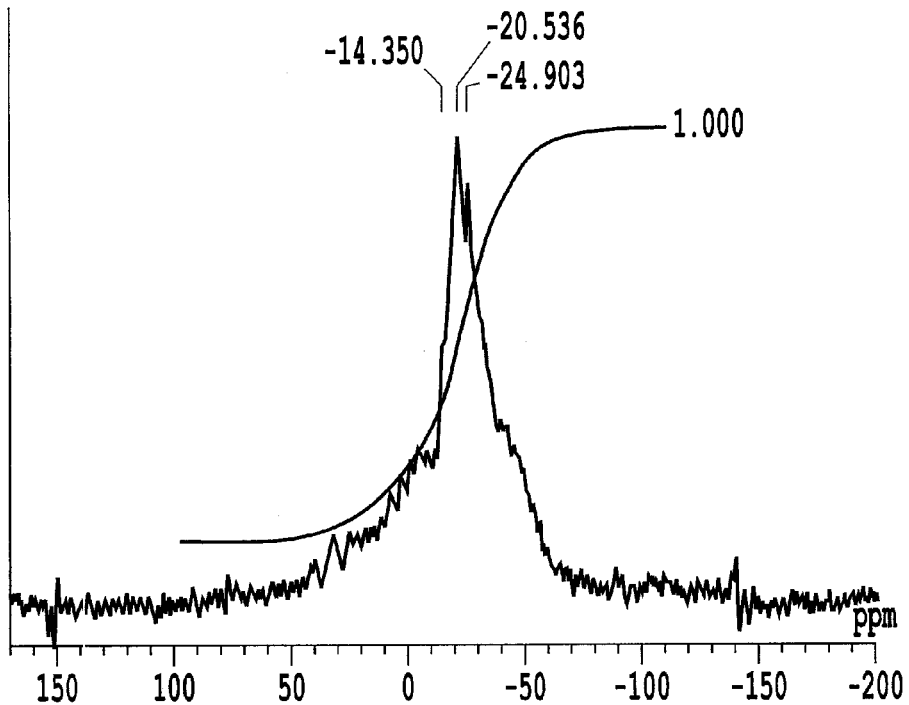
FIG. 1 is a $^{29}$Si MAS-NMR spectrum chart of silicon carbide shaped carrier (a)

Firstly, the catalyst of the present invention will be described in detail.

The catalyst of the present invention contains (1) diamond; (2) at least one species selected from among Group 5 transition element oxides, collectively called oxide A; and (3) at least one species selected from among Group 4 transition element oxides, collectively called oxide B.

(1) Diamond

No particular limitation is imposed on the diamond employed in the catalyst of the present invention, and any of natural products and synthesized products may be employed. In the case of natural products, the place of origin and the quality are not particularly limited. The synthetic products may be synthesized through a conventional method, and the starting material(s) and the synthesis method are not particularly limited.

Examples of known diamond synthesis methods include a synthesis method from graphite under high-temperature/high-pressure conditions (about 1,500° C., about 5 GPa) in the presence of a transition metal such as iron, cobalt, nickel, chromium, manganese, or tantalum; a synthesis method from graphite under higher-temperature/higher-pressure conditions (about 2,000° C., about 7 GPa) in the presence of a carbonate salt, hydroxide, or sulfate salt of an alkali metal element or an alkaline earth metal element; a synthesis method through direct phase-transition of graphite under yet higher-temperature/higher-pressure conditions (about 3,000° C., about 15 GPa) in the absence of catalyst (static high-pressure method); a synthesis method through vapor-phase growth from a carbon-containing compound (e.g., methane or carbon monoxide) and hydrogen gas by the mediation of microwave, high-frequency, heating, etc. (CVD method); and a synthesis method including compressing carbonaceous material by the mediation of explosion of an explosive (explosive synthesis method). Single-crystal or polycrystalline diamond produced through any of the methods may be employed.

No particular limitation is imposed on the morphology of the diamond employed in the present invention, and the diamond employed may have a granular shape, a plate-like shape, a thin flake shape, etc. In the case of granular diamond, no particular limitation is imposed on the grain particle size, so long as the granular diamond can be employed with another material in a catalyst composition or in production of a catalyst. Regardless of natural products or synthetic products, millimeter-size granular diamond is too expensive for use as a catalyst material. Thus, diamond powder, which is supplied at lower cost, is preferably employed. For example, a crashed product of large diamond particles (natural or synthetic) or diamond powder (naturally occurring or synthesized) may be employed. Among them, diamond fine powder having a particle size of 100 μm or less, preferably 10 μm or less, which is widely employed as abrasives, is preferred. A diamond powder in which a portion of 1 wt. % or more has a particle size of 100 μm or less is particularly preferred. Such diamond products are preferred, since they have been generally subjected to, for example, classification or chemical treatment according to the polishing purpose, and are readily available as an industrial commercial product having controlled particle size distribution and impurity level. When the particle size of diamond particles falls within the above ranges, sufficient mixing/dispersing of diamond and oxide(s)

can be attained, whereby a good catalyst can be produced. The particle size of diamond can be readily determined and evaluated by means of, for example, a known laser scattering particle size meter.

No particular limitation is imposed also on the purity of the diamond employed in the present invention. In the cases of natural products and synthetic products, an impurity element other than carbon, which is originating from the atmosphere in which diamond formation has been performed or post treatment, is known to be incorporated into the outer surface or the inside of diamond. Also known is the impurity concentration reaches some thousands ppm or higher in some cases. Although the purity of diamond is preferably higher, a comparatively low purity may also be acceptable. A well-known diamond classification method based on the type of contained impurity, color tone, etc. is a Field's classification (The Properties of Diamond, p. 641, Academic Press (1979)). Any of the types Ia, Ib, IIa, and IIb according to the classification may be used singly and/or in combination.

In the present invention, diamond having high oxidation resistance is preferably used. When the catalyst of the present invention is employed in partial oxidation of an organic compound, the diamond is oxidized slightly, although the diamond is oxidation-resistant as compared with the organic compound. Therefore, the diamond preferably has oxidation resistance in order to prevent loss of diamond due to complete oxidation.

The oxidation resistance of diamond is thought to depend on the amount(s) of boron or transition metal element(s) contained therein and oxidizing functional groups present on the diamond surface. Therefore, the transition metal elements such as Fe, Co, and Ni, serving as impurities are preferably contained in small amounts, since these impurities are thought to catalyze graphitization of diamond at about normal pressure, and formed graphite is thought to have considerably reduced oxidation resistance. Examples of such oxidizable diamond include naturally occurring diamond, diamond synthesized in the presence of a carbonate salt, hydroxide, or sulfate salt of an alkali metal element or an alkaline earth metal element (see Japanese Patent 1995-45652B and NEW DIAMOND, 15 (2), p. 13-19 (1999)), and diamond synthesized through direct phase transition of graphite in the absence of catalyst. The oxidation resistance is known to be enhanced by increasing the boron content of the diamond. For example, boron-containing diamond (see, for example, Japanese Patent 2006-502955A and US Patent Application No. 2004/0018137) is preferably employed. Also, there have been known treatments such as removal of impurities including transition metal elements incorporated into diamond during synthesis or processing (Japanese Patent 1988-303806A, 1997-25110A, 1997-328307A, etc.), and hydrogenation of a diamond surface (see, for example, Bull. Chem. Soc. Jpn. No. 11, p. 631-635 (2001)). Thus, diamond products which have been received such treatments are also preferably employed.

(2) Oxide A

The catalyst of the present invention contains (2) at least one species selected from among Group 5 transition element oxides, collectively called oxide A. Oxide A is preferably, for example, vanadium oxide, niobium oxide, or tantalum oxide. No particular limitation is imposed on the valence of the relevant transition element so long as it falls within the possible range. Among the members of oxide A, those having high valence are preferred for attaining stability in an oxidizing atmosphere and excellent catalytic activity. Examples of preferred such oxides include $VO_2$, $V_2O_5$, $NbO_2$, $Nb_2O_5$, $TaO_2$, and $Ta_2O_5$. Of these, vanadium oxides such as $VO_2$ and $V_2O_5$ are more preferred. Under reaction conditions, at least portion of the oxide may assume more complex valence and crystal phases (e.g., $V_3O_7$, $V_4O_9$, and $V_6O_{13}$). No particular limitation is imposed on the starting materials for forming these oxides, so long as they provide the oxides of interest. For example, a hydroxide, an oxyammonium salt, a chloride, an oxychloride, an oxynitrate salt, an oxalate salt, an oxyoxalate salt, etc. of the element of interest may be employed. These oxides may be used singly or in combination of two or more species.

(3) Oxide B

The catalyst of the present invention contains (3) at least one species selected from among Group 4 transition element oxides, collectively called oxide B. Oxide B is preferably, for example, titanium oxide, zirconium oxide, or hafnium oxide. No particular limitation is imposed on the valence of the relevant transition element so long as it falls within the possible range. Among the members of oxide B, those having high valence are preferred for attaining stability in an oxidizing atmosphere and excellent catalytic activity. Examples of preferred such oxides include $TiO_2$, $ZrO_2$, and $HfO_2$. Of these titanium oxides such as $TiO_2$ are more preferred. No particular limitation is imposed on the starting materials for forming these oxides, so long as they provide the oxides of interest. For example, a hydroxide, a chloride, an oxychloride, an oxysulfate salt, an oxycarbonate salt, a nitrate salt, an oxalate salt, an oxalate ammonium salt, an oxyoxalate ammonium salt, etc. of the element of interest may be employed. These oxides may be used singly or in combination of two or more species.

(4) Oxide C

Preferably, the catalyst of the present invention further contains (4) at least one species selected from among Group 6 transition element oxides, collectively called oxide C. Oxide C is preferably, for example, chromium oxide, molybdenum oxide, or tungsten oxide. No particular limitation is imposed on the valence of the relevant transition element so long as it falls within the possible range. Among the members of oxide B, those having high valence are preferred for attaining stability in an oxidizing atmosphere and excellent catalytic activity. Examples of preferred such oxides include $Cr_2O_3$, $CrO_2$, $CrO_3$, $MoO_2$, $MoO_3$, $WO_2$, and $WO_3$. Of these, chromium oxides such as $Cr_2O_3$, $CrO_2$, and $CrO_3$, and molybdenum oxides such as $MoO_2$ and $MoO_3$ are more preferred. Under reaction conditions, at least portion of the oxide may assume more complex valence and crystal phases (e.g., $Mo_4O_{11}$, $Mo_8O_{23}$, $Mo_9O_{26}$, $W_{18}O_{49}$, and $W_{20}O_{58}$). No particular limitation is imposed on the starting materials for forming these oxides, so long as they provide the oxides of interest. For example, a hydroxide, a chloride, an oxychloride, an oxyacid ammonium salt, a nitrate salt, an acetate salt, an oxalate salt, etc. of the element of interest may be employed. These oxides may be used singly or in combination of two or more species.

(5) Oxide D

Preferably, the catalyst of the present invention further contains (5) at least one species selected from among oxides of the typical elements of Groups 1, 13, 14, 15, and 16, excepting a carbon element, collectively called oxide D.

Group 1 typical element oxides

Examples of preferred Group 1 typical element oxides employed in the catalyst of the present invention include lithium oxide, sodium oxide, potassium oxide, rubidium oxide, and cesium oxide. No particular limitation is imposed on the valence of the relevant transition element so long as it falls within the possible range. Among the oxides of this category, those having high valence are preferred for attaining stability in an oxidizing atmosphere. Examples of preferred such oxides include $Li_2O$, $Na_2O$, $K_2O$, $Rb_2O$, and $Cs_2O$. No particular limitation is imposed on the starting materials for forming these oxides, so long as they provide the oxides of interest. For example, a hydroxide, a chloride, a nitrate salt, an oxalate salt, a carbonate salt, etc. of the element of interest may be employed. These oxides may be used singly or in combination of two or more species.

Group 13 Typical Element Oxides

Examples of preferred Group 13 typical element oxides employed in the catalyst of the present invention include boron oxide, aluminum oxide, gallium oxide, indium oxide, and thallium oxide. No particular limitation is imposed on the valence of the relevant transition element so long as it falls within the possible range. Among the oxides of this category, those having high valence are preferred for attaining stability in an oxidizing atmosphere. Examples of preferred such oxides of the typical element include $B_2O_3$, $Al_2O_3$, $Ga_2O_3$, $In_2O_3$, and $Tl_2O_3$. Of these, boron oxide represented by $B_2O_3$ and aluminum oxide represented by $Al_2O_3$ are more preferred. No particular limitation is imposed on the starting materials for forming these oxides, so long as they provide the oxides of interest. For example, a hydroxide, a chloride, a nitrate salt, an oxalate salt, etc. of the element of interest may be employed. These oxides may be used singly or in combination of two or more species.

Group 14 Typical Element Oxides

Examples of preferred Group 14 typical element oxides employed in the catalyst of the present invention include silicon oxide, germanium oxide, tin oxide, and lead oxide. No particular limitation is imposed on the valence of the relevant transition element so long as it falls within the possible range. Among the oxides of this category, those having high valence are preferred for attaining stability in an oxidizing atmosphere. Examples of preferred such oxides include $SiO_2$, $GeO_2$, $SnO_2$, and $PbO_2$. Of these, germanium oxide represented by $GeO_2$ is more preferred. No particular limitation is imposed on the starting materials for forming these oxides, so long as they provide the oxides of interest. For example, a hydroxide, a chloride, a nitrate salt, an oxalate salt, an acetate salt, etc. of the element of interest may be employed. These oxides may be used singly or in combination.

Group 15 Typical Element Oxides

Examples of preferred Group 15 typical element oxides employed in the catalyst of the present invention include phosphorus oxide, antimony oxide, and bismuth oxide. No particular limitation is imposed on the valence of the relevant transition element so long as it falls within the possible range. Among the oxides of this category, those having high valence are preferred for attaining stability in an oxidizing atmosphere. Examples of preferred such oxides include $P_2O_5$, $Sb_2O_4$, $Sb_2O_5$, $Bi_2O_4$, and $Bi_2O_5$. Of these, phosphorus oxide represented by $P_2O_5$ and antimony oxides such as $Sb_2O_4$ and $Sb_2O_5$ are more preferred. No particular limitation is imposed on the starting materials for forming these oxides, so long as they provide the oxides of interest. For example, a hydroxide, a chloride, an oxychloride, an oxyammonium salt, a nitrate salt, an oxalate salt, an acetate salt, an oxyacetate salt, etc. of the element of interest may be employed. These oxides may be used singly or in combination Group 16 Typical Element Oxides Examples of preferred Group 16 typical element oxides employed in the catalyst of the present invention include selenium oxide and tellurium oxide. No particular limitation is imposed on the valence of the relevant transition element so long as it falls within the possible range. Among the oxides of this category, those having high valence are preferred for attaining stability in an oxidizing atmosphere. Examples of preferred such oxides include $TeO_2$, $TeO_3$, and $SeO_2$. Of these, tellurium oxides such as $TeO_2$ and $TeO_3$ are more preferred. No particular limitation is imposed on the starting materials for forming these oxides, so long as they provide the oxides of interest. For example, a hydroxide, an oxyammonium salt, a chloride, an oxychloride, an oxynitrate salt, etc. of the element of interest may be employed. These oxides may be used singly or in combination.

Each of the oxides A to D employed in the catalyst of the present invention may be amorphous or crystalline. When a member of the oxides has some polymorphs, one single type or a mixture of polymorphs may be employed. Specifically, in the case of titanium dioxide, the oxide of a formula $TiO_2$ is known to have three polymorphs crystal types (rutile, anatase, and brookite). Any one of the structure types or two or more types (solid solutions, twin crystals, and mixtures) selected therefrom may be employed.

Oxides A to D employed in the catalyst of the present invention may be a mixture of individual components, or at least a part of the oxides contained as catalyst components may form a complex oxide. When the catalyst of the present invention employs vanadium oxide serving as oxide A for partial oxidation of an organic compound, catalytic activity may be remarkably enhanced through use in combination with other oxides serving as a co-catalyst component. When vanadium oxide and other oxides are used in combination, the composition of the components at an effective catalytically active site under reaction conditions has not been elucidated in detail. However, at least a portion of vanadium oxide is thought to form a complex oxide phase with other oxide components such as titanium oxide, chromium oxide, and molybdenum oxide, whereby catalytic activity and reaction selectivity can be enhanced. In the present invention, addition of diamond to these catalyst components is thought to further enhance catalytic activity. When a complex oxide phase is formed, the phase may assume a specific crystal structure including of a plurality of oxides (e.g., heteropoly-acids). In this case, when a complex oxide has some polymorphs, any one of the structure types or two or more types (solid solutions, twin crystals, and mixtures) selected therefrom may be employed.

Composition of Catalyst

Preferably, the catalyst of the present invention contains vanadium oxide serving as oxide A, and titanium oxide serving as oxide B. In the case where the catalyst of the present invention contains oxide C, preferably, oxide A is vanadium oxide, oxide B is titanium oxide, and oxide C is at least one species selected from molybdenum oxide and chromium oxide.

In the catalyst of the present invention, oxide D is preferably at least one species selected from among oxides of boron, aluminum, germanium, phosphorus, antimony, and tellurium, more preferably from boron and phosphorus.

No particular limitation is imposed on the diamond content of the catalyst of the present invention, and the diamond content is preferably 0.1 parts by weight (unless otherwise specified, the unit "part(s) by weight is referred to as simply "part(s)") or more, with respect to 100 parts (total amount) of oxides A and B in the catalyst (when the catalyst contains oxide C, with respect to 100 parts (total amount) of oxides A to C), more preferably 1 part or more, still more preferably 3 parts or more, particularly preferably 5 parts or more. The present inventors previously confirmed that diamond itself does not have strong oxidizing ability, and that addition of diamond in an increased amount larger than the required level does not impair catalytic activity. However, use of an excessive amount of diamond problematically increases catalyst production cost. Therefore, the diamond content with respect to 100 parts (total amount) of oxides A and B in the catalyst (when the catalyst contains oxide C, with respect to 100 parts (total amount) of oxides A to C) is preferably 200 parts or less, more preferably 100 parts or less, still more preferably 50 parts or less, particularly preferably 10 parts or less.

In the present invention, the total weight of oxide A with respect to the total weight of the aforementioned oxides (oxides A and B, oxides A to C, or oxides A to D) is preferably 0.5 to 50 wt. %, more preferably 1 to 20 wt. %. The total weight of oxide B is preferably 1 to 99 wt. %, more preferably 70 to 99 wt. %. The total weight of oxide C is preferably 0 to 50 wt. %, more preferably 1 to 10 wt. %. The total weight of oxide D is preferably 0 to 50 wt. %, more preferably 0.5 to 10 wt. %. Notably, in each case, the total weight of the aforementioned oxides is 100 wt. %. Although the ratio of diamond to the total weight of transition element oxides A and B or oxides A to C has a preferred value, no particular limitation is imposed on the other ratios between the oxide components, so long as the ratios fall within the aforementioned compositional ranges.

Method of Producing Catalyst

In partial oxidation catalysts, a variety of components were added to the catalyst in order to enhance reaction selectivity. Such catalysts attaining higher selectivity tend to contain a larger number of components. Increase in the number of components possibly causes problems, including cumbersome preparatory operation (e.g., blending a plurality of starting materials) and preliminary treatment operations as well as limited catalyst compositional ranges and reaction conditions for attaining optimum reaction results. However, diamond is less likely to cause such problems, since it has very high physical and chemical stability, and is not readily deteriorated through reaction with other components, and is not readily converted to different crystal phase under generally employed catalyst preparation conditions. Regarding diamond, no particular limitation is imposed on the conditions of treatment during and after the addition and the storage conditions, making diamond easily employed as an additive having a wide range of adaptability. Therefore, needless to say, conventionally known catalyst production methods may be applied to production of the catalyst of the present invention. Particularly, methods as disclosed in the aforementioned patent documents may be employed. In some cases, the catalyst composition of the present invention can be produced through addition of only diamond, which is added to a conventional production scheme, without modifying a step thereof.

As described above, no particular limitation is imposed on the method for producing the diamond-containing catalyst of the present invention. According to the studies by the present inventors, higher catalytic activity or reaction selectivity tends to be attained by a sufficiently dispersed/mixed state of diamond and other metal oxides in the catalyst. Therefore, such a production method which can produce a well-dispersed mixture is particularly preferred.

In order to attain a sufficient dispersion/mixing state, an operation including adding diamond fine particles to other starting materials (oxide components) and sufficient agitating and mixing is performed during the catalyst preparation process. Such an operation can readily be performed. Examples of such catalyst production methods employing the operation includes: (a) a method including adding diamond fine powder to a homogeneous aqueous solution containing water-soluble materials of oxide components, sufficiently stirring the mixture to form a suspension, forming a precursor through evaporation of water (solvent) or co-precipitation with an appropriate precipitating agent, and converting the precursor to a diamond-containing oxide mixture through, for example, calcinating; (b) a method including adding a part of oxide components and diamond fine powder to a homogeneous aqueous solution containing a water-soluble material of a part of oxide components, sufficiently stirring the mixture to form a suspension, forming a precursor through evaporation of water (solvent) or co-precipitation with an appropriate precipitating agent, and converting the precursor to a diamond-containing oxide mixture through, for example, calcinating; and (c) a method including growing a diamond layer on vanadium oxide through CVD to form a catalyst-on-carrier, which method employs diamond and Group 5 transition element oxides in combination and disclosed in the document (Ind. Eng. Chem. Res., 32, 263-273 (1993)). Among these methods, catalyst preparation methods (a) and (b) are preferred, from the viewpoint that since higher catalytic activity can be attained in the case where diamond and other metal oxides are sufficiently dispersed and mixed in the catalyst.

The catalyst of the present invention may be employed in the reaction without a carrier, when the catalyst itself is formed into particles or is shaped. Formation of particles and shaping may be performed through a known method. Examples of such catalyst production methods include (d) a method including adding diamond fine powder to a homogeneous aqueous solution containing water-soluble materials of oxide components, sufficiently stirring the mixture to form a suspension, spraying the suspension to form a granular precursor, and forming a particulate catalyst of a diamond-containing oxide mixture through, for example, calcinating; (e) a method including adding diamond fine powder to a homogeneous aqueous solution containing water-soluble materials of oxide components, sufficiently stirring the mixture to form a suspension, forming a precursor through evaporation of water (solvent) or co-precipitation with an appropriate precipitating agent, shaping the precursor through pelletizing, extruding, granulating, etc., and forming a shaped catalyst of a diamond-containing oxide mixture through, for example, calcinating; (f) a method including evaporating water (solvent) from a homogeneous solution containing water-soluble materials of a part of oxide components or adding an appropriate precipitating agent to the solution, to form a precursor, adding a part of oxide components and diamond fine powder to the precursor, followed by sufficient kneading, shaping the precursor mixture through pelletizing, extruding, granulating, etc., and forming a shaped catalyst of a diamond-containing oxide mixture through, for example, calcinating; and (g) a method including adding diamond fine powder to a homogeneous aqueous solution containing water-soluble materials of oxide components, sufficiently stirring the mixture to form a suspension, forming a precursor through evaporation of water (solvent) or co-precipitation with an appropriate precipitating agent, converting the precursor to a diamond-containing oxide mixture through, for example, calcinating, and shaping the mixture through pelletizing, extruding, granulating, etc., to thereby form a shaped catalyst.

In the present invention, the shape and particle size distribution of granules, the shape and dimensions of shaped products, etc. may be the same as employed in known methods, so long as these properties are suited for the reaction. When a shaped catalyst is employed, the shape is preferably spherical, cylindrical, ring-shape, etc.

Catalyst-on-Carrier

The catalyst of the present invention may be employed in the reaction in the form of a catalyst-on-carrier in which the catalyst is supported on a carrier inert to the reaction. No particular limitation is imposed on the material of the carrier, and known materials may be used. Examples of preferred carrier materials include silicon carbide, alumina, silica, zirconia, steatite, cordierite, mullite, porcelain, and ceramics. The catalyst-on-carrier of the present invention preferably employs a shaped carrier containing at least one species selected from the mentioned carrier materials. No particular limitation is imposed on the shape of the carrier, and carriers having a known shape (spherical, cylindrical, ring-shape, etc.) are preferably employed. No particular limitation is imposed on the property (e.g., size, porosity, or BET specific surface area) of the carrier, and those carriers suitable for partial oxidation as employed in known methods may also be employed.

No particular limitation is imposed on the method of impregnating the catalyst composition of the present invention on a carrier, and a known method may be employed. As described above, the impregnating method is preferably selected so that a sufficiently dispersed and mixed state of diamond and other metal oxides is attained in the catalyst. From this viewpoint, examples of preferred impregnating methods include (h) a method including adding diamond fine powder to a homogeneous aqueous solution containing water-soluble materials of oxide components, sufficiently stirring the mixture to form a suspension, spraying the suspension to a carrier, and forming a catalyst in which a diamond-containing oxide mixture has been caused to be supported on the carrier through, for example, calcinating; and (i) a method including adding a part of oxide components and diamond fine powder to a homogeneous aqueous solution containing a water-soluble material of a part of oxide components, sufficiently stirring the mixture to form a suspension, spraying the suspension to a carrier, and forming a catalyst in which a diamond-containing oxide mixture has been caused to be supported on the carrier through, for example, calcinating.

In the catalyst-on-carrier of the present invention, the amount of catalyst impregnated by the catalyst-on-carrier is preferably 0.1 to 20 wt. % with respect to the total weight of the catalyst-on-carrier, more preferably 0.5 to 15 wt. %, still more preferably 1 to 10 wt. %. When the catalyst amount is 20 wt. % or less, removal of carrier components is prevented, whereas when the catalyst amount is 0.1 wt. % or more, sufficient catalytic activity can be attained. Both cases are preferred.

Use of Catalyst

The catalyst of the present invention is suitably employed in vapor-phase partial oxidation of an organic compound. The organic compound includes a C1 to C20 saturated aliphatic hydrocarbon, an unsaturated aliphatic hydrocarbon, an aromatic hydrocarbon, a heterocyclic compound, an alcohol compound, an aldehyde compound, a ketone compound, an ether compound, an ester compound (including a lactone compound), and an oxygen-containing intermediate which is formed through partial oxidation of a part of carbon atoms in any of the compounds to a carboxyl group. No particular limitation is imposed on the species of the organic compound, so long as the vapor of the compound undergoes partial oxidation on the catalyst. These specific organic compounds may be used singly or in combination or two or more species. When two or more different organic compounds are used, no particular limitation is imposed on the mixing ratio.

Specific examples of the organic compounds to which the catalyst of the present invention is applicable will be next be given.

Saturated Aliphatic Hydrocarbon

No particular limitation is imposed on the type of the saturated aliphatic hydrocarbon, so long as it is a linear, branched, or cyclic alkane. Specific examples include methane, ethane, propane, n-butane, isobutane, 2-methylbutane, 2,2-dimethylbutane, n-hexane, 2,2,4-trimethylpentane, cyclopentane, cyclohexane, and decalin.

Unsaturated Aliphatic Hydrocarbon

No particular limitation is imposed on the type of the unsaturated aliphatic hydrocarbon, so long as it is an unsaturated compound derived through converting at least one C—C single bond of a linear, branched, or cyclic alkane to a C=C double bond. In the case of such a compound having two or more double bonds, these double bonds may or may not necessarily be conjugated. When the compound has a geometrical isomer, each of the isomers or a mixture thereof may be employed. Examples of the unsaturated aliphatic hydrocarbon include ethylene, propylene, 1-butene, 2-butene, isobutene, 1,3-butadiene, 2-methyl-1,3-butadiene, 1-hexene, 1,5-hexadiene, cyclopentene, cyclopentadiene, and cyclohexene.

Aromatic Hydrocarbon

No particular limitation is imposed on the type of the aromatic hydrocarbon, so long as it is a compound having at least one aromatic ring. The aromatic ring may have a linear, branched, or cyclic alkyl group or alkenyl group. When the compound has a plurality of aromatic rings, these rings may be condensed or directly bonded to one another. Alternatively, these rings may be bonded to one another via at least one carbon chain outside the ring. Examples of the aromatic hydrocarbon include benzene, toluene, ethylbenzene, n-propylbenzene, i-propylbenzene, n-butylbenzene, o-xylene, m-xylene, p-xylene, 1,2,4-trimethylbenzene, 1,2,4,5-tetramethylbenzene, 1,2,4,5-tetraethylbenzene, 6,7-dimethyl-1,2,3,4-tetrahydronaphthalene, styrene, i-propenylbenzene, stilbene, tetralin, naphthalene, 1-methylnaphthalene, 2-methylnaphthalene, 1,4-dimethylnaphthalene, 1,5-dimethylnaphthalene, 2,3-dimethylnaphthalene, 2,6-dimethylnaphthalene, 2,6-diethylnaphthalene, 2,6-di-i-propylnaphthalene, 2,7-dimethylnaphthalene, 1-acetylnaphthalene, 2-acetylnaphthalene, anthracene, 1,2,3,4-tetrahydroanthracene, 1,2,3,4,5,6,7,8-octahydroanthracene, biphenyl, 4-methylbiphenyl, 4,4'-dimethylbiphenyl, 4,4'-dimethylbiphenyl, 4,4'-diethylbiphenyl, 4,4'-di-i-propylbiphenyl, cyclohexylbenzene, diphenylmethane, triphenylmethane, 1,2-diphenylethane, 1,2-bis-(2,4,5-trimethylphenyl)-ethane, indene, 5,6-dimethyl-1H-indene, 5,6-dimethyl-2,3-dihydro-1H-indene, indane, s-indacene, and 1,2,3,5,6,7-hexahydro-s-indacene.

Heterocyclic Compound

No particular limitation is imposed on the type of the heterocyclic compound, so long as it is a compound having at least one heterocyle. The heterocycle may have a linear, branched, or cyclic alkyl or alkenyl group or an aryl group. When the compound has a plurality of heterocycles, these rings may be condensed or directly bonded to one another. Alternatively, these rings may be bonded to one another via at least one carbon chain outside the ring. Examples of the heterocyclic compound include oxirane, oxetane, furan, 3-methylfuran, tetrahydrofuran, 3-methyltetrahydrofuran, pyran, tetrahydropyran, dioxane, azilidine, azetidine, pyrrole, pyrrolidine, piperidine, pyridine, pyrazine, piperazine, 2-methylpyridine, 2-methyl-5-ethylpyridine, 3-methylpyridine, 4-methylpyridine, 2-methylpyrazine, imidazole, oxazole, morpholine, isobenzofuran, phthalan, isochromene, and isochromane.

Alcohol Compound

No particular limitation is imposed on the type of the alcohol compound, so long as it is a compound selected from the aforementioned saturated aliphatic hydrocarbon, unsaturated aliphatic hydrocarbon, aromatic hydrocarbon, and heterocyclic compound in which at least one C—H bond has been converted to a C—OH bond (hydroxyl group). Examples of the alcohol compound include methanol, ethanol, 1-propanol, isopropanol, 1-butanol, isobutanol, neopentanol, allyl alcohol, crotyl alcohol, methallyl alcohol, 1,3-propylene glycol, 1,4-butanediol, neopentyl glycol, pinacol, cyclopentanol, cyclohexanol, benzyl alcohol, cumyl alcohol, 2-methylbenzyl alcohol, 3-methylbenzyl alcohol, 4-methylbenzyl alcohol, 3,4-dimethylbenzyl alcohol, 2,4-dimethylbenzyl alcohol, 2,4,5-trimethylbenzyl alcohol, benzhydrol, and phenethyl alcohol.

Aldehyde Compound

No particular limitation is imposed on the type of the aldehyde compound, so long as it is a compound selected from the aforementioned saturated aliphatic hydrocarbon, unsaturated aliphatic hydrocarbon, aromatic hydrocarbon, and heterocyclic compound in which at least one end methyl ($CH_3$) group has been converted to a formyl (CHO) group. Examples of the aldehyde compound include formaldehyde, acetaldehyde, propionaldehyde, n-butylaldehyde, capraldehyde, acrolein, methacrolein, crotonaldehyde, succinaldehyde, malealdehyde, glutaraldehyde, benzaldehyde, o-tolualdehyde, m-tolualdehyde, p-tolualdehyde, p-ethylbenzaldehyde, p-i-propylbenzaldehyde, phthalaldehyde, isophthalaldehyde, terephthalaldehyde, 3,4-dimethylbenzaldehyde, 2,4-dimethylbenzaldehyde, 2,4,5-trimethylbenzaldehyde, 1-naphthylaldehyde, 2-naphthylaldehyde, 1-naphthylacetaldehyde, biphenyl-4-carbaldehyde, 4'-methylbiphenyl-4-carbaldehyde, nicotinaldehyde, phenylacetaldehyde, and cinnamaldehyde.

Ketone Compound

No particular limitation is imposed on the type of the ketone compound, so long as it is a compound selected from the aforementioned saturated aliphatic hydrocarbon, unsaturated aliphatic hydrocarbon, aromatic hydrocarbon, and heterocyclic compound in which at least one methylene ($CH_2$) group has been converted to a carbonyl (C=O) group. Examples of the aldehyde compound include acetone, 2-butanone, 2-pentanone, pinacolone, 2-hexanone, 2,3-butanedione, 2,4-pentanedione, cyclopentanone, cyclohexanone, methyl vinyl ketone, mesityl oxide, 1-phenyl-ethanone, 1-o-tolyl-ethanone, 1-m-tolyl-ethanone, 1-p-tolyl-ethanone, 1-(2,4-dimethylphenyl)-ethanone, 1-(2,5-dimethylphenyl)-ethanone, 1-(2,4,5-trimethylphenyl)-ethanone, benzophenone, benzil, 1-naphthalenone, inden-1-one, fluorenone, 1,4-naphthoquinone, 6,7-dimethyl-1,4-naphthoquinone, 9,10-anthraquinone, 2,3,7,8-tetramethyl-9,10-anthraquinone, anthracene-1,4-dione, and anthracene-1,4,5,8-tetraone.

Ether Compound

No particular limitation is imposed on the type of the ether compound, so long as it is a compound selected from the aforementioned saturated aliphatic hydrocarbon, unsaturated aliphatic hydrocarbon, aromatic hydrocarbon, and heterocyclic compound in which at least one methylene ($CH_2$) group has been converted to an ether (—O—) bond. Examples of the ether compound include dimethyl ether, diethyl ether, dipropyl ether, cyclopentyl methyl ether, cyclohexyl methyl ether, benzylmethyl ether, diallyl ether, allyl methyl ether, methallyl methyl ether, 1,1-dimethoxyethane, 1,1-dimethoxypropane, methoxymethylbenzene, 1-methoxymethyl-2-methylbenzene, 1-methoxymethyl-3-methylbenzene, 1-methoxymethyl-4-methylbenzene, 1-methoxymethyl-2,4-dimethylbenzene, 1-methoxymethyl-2,4,5-trimethylbenzene, 1-dimethoxymethyl-2-methylbenzene, 1-dimethoxymethyl-3-methylbenzene, 1-dimethoxymethyl-4-methylbenzene, and 1-dimethoxymethyl-2,4,5-trimethylbenzene.

Ester Compound

No particular limitation is imposed on the type of the ester compound (including lactone compound), so long as it is a compound selected from the aforementioned saturated aliphatic hydrocarbon, unsaturated aliphatic hydrocarbon, aromatic hydrocarbon, and heterocyclic compound in which at least one methylene ($CH_2$) group has been converted to an ester (—C(=O)O—) bond. Examples of the ester compound include allyl acetate, butyl acetate, isobutyl acetate, methallyl acetate, methyl butyrate, methyl crotonate, β-propiolactone, γ-butyrolactone, α-methyl-γ-butyrolactone, ε-caprolactone, methyl 2-methylbenzoate, methyl 2,4-dimethylbenzoate, methyl 3,4-dimethylbenzoate, dimethyl 4-methylphthalate, dimethyl 4-methylisophthalate, dimethyl 5-methylisophthalate, dimethyl 2-methylterephthalate, methyl 2,4,5-trimethylbenzoate, dimethyl 4,5-dimethylphthalate, dimethyl 4,6-dimethylisophthalate, dimethyl 2,5-dimethylterephthalate, trimethyl 5-methyltrimellitate, methyl 6-methylnaphthalene-2-carboxylate, methyl 5-methylnaphthalene-1-carboxylate, methyl 4'-methyl-biphenyl-4-carboxylate, phthalide, methyl phthalide, and dimethyl phthalide.

Other Species

In oxidation reaction of an organic compound, it is thought that an oxygen-containing intermediate has, in a molecule thereof, a plurality of carbon atoms in different oxidation states. A possible mechanism of forming such an intermediate is that different sites in the molecule are simultaneously oxidized at a plurality of active sites of the employed solid catalyst, or that a certain site of the organic compound molecule is successively oxidized, with oxidation of another site starting during transfer of the compound on the catalyst layer. Needless to say, in the present invention, such an intermediate may be employed as a starting substance for forming carboxylic acid.

Examples of such an oxygen-containing intermediate include compounds derived through simultaneous substitution of the aforementioned organic compounds at a plurality of sites with two or more groups selected from among a hydroxyl group, a formyl group, a carbonyl group, an ether bond, and ester group; and compounds having a carboxyl group formed through oxidation of a part of the carbon atoms and a carbon atom which can be oxidized to a carboxyl group in the molecule (i.e., carboxylic acid compounds). In the case where a part of the carbon atoms has been oxidized to a carboxyl group, the formed carboxyl group may be linked to another functional group in the vicinity thereof. For example, the carboxyl group may be dehydrated with another carboxyl group in the vicinity thereof, to thereby form a carboxylic anhydride, or may be dehydrated with a hydroxyl group in the vicinity thereof, to thereby form a lactone compound. Specific examples of such an intermediate include propionic acid, acrylic acid, butanoic acid, isobutanoic acid, methacrylic acid, 3-butenoic acid, 2-butenoic acid, 4-hydroxy-butylaldehyde, 4-hydroxybutanoic acid, 4-hydroxy-2-butenoic acid, methyl 4-hydroxybutanoate, 4-oxo-butane acid, 4-oxo-2-butenoic acid, malonaldehyde acid, adipaldehyde acid, 2-formyl-benzyl alcohol, 3-formyl-benzyl alcohol, 4-formyl-benzyl alcohol, phthalaldehyde acid, isophthalaldehyde acid, terephthalaldehyde acid, o-toluic acid, m-toluic acid, p-toluic acid, 3,4-dimethylbenzoic acid, 2,4-dimethylbenzoic acid, 3,5-dimethylbenzoic acid, 2,4,5-trimethylbenzoic acid, 4-methylphthalic acid, 4-methylisophthalic acid, 5-methylisophthalic acid, 2-methylterephthalic acid, 4,5-dimethylphthalic acid, 4,6-dimethylisophthalic acid, 2,5-dimethylterephthalic acid, 5-methyltrimellitic acid, 6-methylnaphtalene-2-carboxylic acid, 5-methylnaphtalene-1-carboxylic acid, 4'-formyl-biphenyl-4-carboxylic acid, 4'-methyl-biphenyl-4-carboxylic acid, phthalic anhydride, methylphthalic anhydride, dimethylphthalic anhydride, and pyrromeride (7H-benzo[1,2-c; 4,5-c']difuran-1,3,5-trione).

The catalyst of the present invention exhibits excellent performance particularly in, among the aforementioned organic compounds, an aromatic compound having one or more substituents in a molecule thereof, the substituents each including a carbon atom bonded to an aromatic ring. Therefore, the catalyst is preferably employed in such oxidation reaction.

Method for Producing Carboxylic Acid or Carboxylic Anhydride

A characteristic feature of the method of the present invention for producing a carboxylic acid or a carboxylic anhydride resides in that an organic compound is subjected to vapor phase partial oxidation by use of an oxygen-containing gas in the presence of the aforementioned catalyst, wherein the organic compound is an aromatic compound having one or more substituents in a molecule thereof, the substituents each including a carbon atom bonded to an aromatic ring. As used herein, the term "partial oxidation" refers to oxidation of at least one carbon atom of a starting substance to a carboxyl group. The formed carboxylic acid may be monocarboxylic acid or polycarboxylic acid. The molecular skeleton of the starting substance is not necessarily maintained. In the case where the skeleton is not maintained, a lower carboxylic acid having carbon atoms less than that of the starting substance may be formed through decomposition and/or combustion. In some cases, a plurality of lower carboxylic acids may be formed, or the amount of formed lower carboxylic acid may exceed the amount by mole of the starting substance. Such reaction features are briefly described in, for example, British Patent No. 1,165,442 (Examples) (formation of formic acid, acetic acid, propionic acid, and maleic acid through vapor-phase partial oxidation of butenes) and Japanese Patent 1981-12637B (formation of pyromellitic dianhydride through vapor-phase partial oxidation of 1,2-bis-(2,4,5-trimethylphenyl)-ethane).

The saturation degree of the carbon atom of the starting substance which atom is not converted to a carboxyl group may or may not be maintained. In the case where saturation is not maintained, a higher carboxylic acid may be formed through decomposition and/or combustion. Such reaction features are briefly described in, for example, WO 06/100128 (pamphlet) (formation of acrylic acid through phase partial oxidation of propane).

The formed carboxyl group may be linked to another functional group in the vicinity thereof. For example, when two carboxyl groups are present close to each other, through partial oxidation, the two carboxyl groups form carboxylic anhydride through dehydration, or the carboxyl group formed through partial oxidation and a hydroxyl group in the vicinity thereof are form a lactone. The production method of the present invention also encompasses such cases. Notably, when two carboxyl groups are present close to each other, one carboxyl group may be originally present in the starting substance, and the other carboxyl group may be formed through partial oxidation. Also, the hydroxyl group in the vicinity of the formed carboxyl group may be originally present in the starting substance or may be formed through partial oxidation. Such reaction features are briefly described in, for example, Japanese Patent 1974-41271B (Examples) (formation of phthalic anhydride (carboxylic anhydride) and a phthalide (a lactone compound) through partial oxidation of o-xylene).

Organic Compound

In the production method of the present invention, the organic compound employed as a starting material is an aromatic compound having one or more substituents in a molecule thereof, the substituents each including a carbon atom bonded to an aromatic ring. According to the production method of the present invention, by use of the catalyst of the present invention, an aromatic carboxylic acid or an aromatic carboxylic anhydride (hereinafter may be collectively referred to as aromatic carboxylic acid) can be formed through partial oxidation of a substituent to form a side-chain carboxyl group while the aromatic ring is maintained. The thus-produced aromatic carboxylic acids are useful industrial materials for a variety of applications.

Hereinafter, the organic compound employed as a starting compound in the production method of the present invention will be described in detail.

The organic compound employed as a starting compound in the production method of the present invention for forming an aromatic carboxylic acid is an aromatic compound which has at least one aromatic ring and one or more (preferably two or more) substituents in a molecule thereof, the substituents each including a carbon atom bonded to an aromatic ring. The aromatic compound preferably has 7 to 20 carbon atoms. In the present invention, the aromatic ring include a monocyclic ring, a condensed polycyclic ring, and a condensed heterocycle having at least one aromatic ring.

Examples of the substituent having a carbon atom bonded to an aromatic ring include alkyl group such as methyl, ethyl, and propyls (n-propyl and i-propyl); alkenyl groups such as vinyl and propenyl; acyl groups such as formyl, acetyl, and propionyl; groups formed through substitution of at least one hydrogen atom of these alkyl, alkenyl, and acyl groups with a hydroxyl group or an alkoxy group; and groups formed through substitution of at least one carbon atom of these alkyl, alkenyl, and acyl groups with a formyl group, a carbonyl group, or an ester group. Among these groups, methyl, ethyl, propyl, acetyl, and formyl are preferably employed. The substituent is preferably at least one member selected from the five groups.

The substituent may be linked to another site of the same aromatic ring to form a ring structure. When the starting compound has a plurality of aromatic rings in a molecule thereof, these rings may be condensed or directly bonded to one another. Alternatively, these rings may be bonded to one another via at least one carbon chain outside the ring. For example, as described hereinbelow, compounds such as biphenyl and naphthalene are also included in the aromatic compound employed in the present invention. When the starting compound has a plurality of substituents in a molecule thereof, these substituents may be identical to or different from one another, and the locants thereof are not particularly limited. When the starting compound has a plurality of aromatic rings, the locants thereof are not particularly limited.

Examples of the Organic Compound

The aromatic compound employed in the present invention include (i) oxygen-containing intermediates formed through partial oxidation of a part of carbon atoms in the compound to form a carboxyl group; (ii) oxygen-containing intermediates having, in a molecule thereof, a plurality of carbon atoms in different oxidation states; the intermediate of the two types being gives as examples of the organic compound to which the catalyst of the present invention can be applied, and (iii) oxygen-containing intermediates formed through partial oxidation of all the substituents to form side-chain carboxyl groups. Examples of the case (iii) include aromatic compounds each having a side-chain carboxyl group formed through oxidation of at least one substituent, and a substituent which can be oxidized to a carboxyl group in the molecule. The thus-formed carboxyl group may be linked to another functional group in the vicinity thereof. For example, the carboxyl group may be dehydrated with another carboxyl group in the vicinity thereof, to thereby form a carboxylic anhydride, or may be dehydrated with a hydroxyl group in the vicinity thereof, to thereby form a lactone compound.

No particular limitation is imposed on the aromatic compound employed in the present invention, so long as the vapor of the compound selected from the above-exemplified members undergoes partial oxidation on the catalyst. These aromatic compounds may be used singly or in combination of two or more species. When two or more species are employed, no particular limitation is imposed on the ratio (proportions) of the compounds.

Specific examples of the aromatic compound employed in the present invention will next be given.

Examples of the aromatic compound include:

monocyclic aromatic compounds such as toluene, ethylbenzene, n-propylbenzene, i-propylbenzene, n-butylbenzene, o-xylene, m-xylene, p-xylene, 1,2,4-trimethylbenzene, 1,2,4,5-tetramethylbenzene, 1,2,4,5-tetraethylbenzene, tetralin, 6,7-dimethyl-1,2,3,4-tetrahydronaphthalene, styrene, i-propenylbenzene, o-toluic acid, m-toluic acid, p-toluic acid, 4-ethylbenzoic acid, 4-i-propylbenzoic acid, 3,4-dimethylbenzoic acid, 2,4-dimethylbenzoic acid, 3,5-dimethylbenzoic acid, 2,4,5-trimethylbenzoic acid, 4-methylphthalic acid, 4-methylisophthalic acid, 5-methylisophthalic acid, 2-methylterephthalic acid, 4,5-dimethylphthalic acid, 4,6-dimethylisophthalic acid, 2,5-dimethylterephthalic acid, 5-methyltrimellitic acid, methylphthalic anhydride, and dimethylphthalic anhydride;

monocyclic aromatic compounds having a plurality of aromatic rings such as stilbene biphenyl, 4-methylbiphenyl, 4,4'-dimethylbiphenyl, 4,4'-diethylbiphenyl, 4,4'-di-i-propylbiphenyl, cyclohexylbenzene, diphenylmethane, triphenylmethane, 1,2-diphenylethane, 1,2-bis-(2,4,5-trimethylphenyl)-ethane, 4'-formyl-biphenyl-4-carboxylic acid, and 4'-methylbiphenyl-4-carboxylic acid;

condensed polyheterocyclic aromatic compounds having a condensed (aromatic-aromatic) aromatic ring such as naphthalene, 1-methylnaphthalene, 2-methylnaphthalene, 1,5-dimethylnaphthalene, 1,4-dimethylnaphthalene, 2,3-dimethylnaphthalene, 2,6-dimethylnaphthalene, 2,6-diethylnaphthalene, 2,6-di-i-propylnaphthalene, 2,7-dimethylnaphthalene, anthracene, 1,2,3,4-tetrahydroanthracene, 1,2,3,4,5,6,7,8-octahydroanthracene, 5,6-dimethyl-1H-indene, 5,6-dimethyl-2,3-dihydro-1H-indene, 6-methylnaphthalene-2-carboxylic acid, and 5-methylnaphthalene-1-carboxylic acid;

heterocyclic compounds such as indene, indane, s-indacene, 1,2,3,5,6,7-hexahydro-s-indacene, acenaphthene, isobenzofuran, phthalan, isochromene, isochromane, and pyrromeride (7H-benzo[1,2-c; 4,5-c']difuran-1,3,5-trione);

alcohol compounds such as benzyl alcohol, cumyl alcohol, 2-methylbenzyl alcohol, 3-methylbenzyl alcohol, 4-methylbenzyl alcohol, 3,4-dimethylbenzyl alcohol, 2,4-dimethylbenzyl alcohol, 2,4,5-trimethylbenzyl alcohol, benzhydrol, phenethyl alcohol, 2-formyl-benzyl alcohol, 3-formyl-benzyl alcohol, and 4-formyl-benzyl alcohol;

aldehyde compounds such as benzaldehyde, o-tolualdehyde, m-tolualdehyde, p-tolualdehyde, p-ethylbenzaldehyde, p-i-propylbenzaldehyde, 3,4-dimethylbenzaldehyde, 2,4-dimethylbenzaldehyde, 2,4,5-trimethylbenzaldehyde, phthalaldehyde, isophthalaldehyde, terephthalaldehyde, phenylacetaldehyde, cinnamaldehyde, 1-naphthylaldehyde, 2-naphthylaldehyde, 1-naphthylacetaldehyde, biphenyl-4-carbaldehyde, 4'-methylbiphenyl-4-carbaldehyde, phthalaldehyde acid, isophthalaldehyde acid, and terephthalaldehyde acid;

ketone compounds such as 1-phenyl-ethanone, 1-phenyl-propanone, 1-o-tolyl-ethanone, 1-m-tolyl-ethanone, 1-p-tolyl-ethanone, 1-(2,4-dimethylphenyl)-ethanone, 1-(2,5-dimethylphenyl)-ethanone, 1-(2,4,5-trimethylphenyl)-ethanone, benzophenone, benzil, 1-naphthalenone, inden-1-one, fluorenone, 1,4-naphthoquinone, 6,7-dimethyl-1,4-naphthoquinone, 9,10-anthraquinone, 2,3,7,8-tetramethyl-9,10-anthraquinone, anthracene-1,4-dione, anthracene-1,4,5,8-tetraone, 1-acetylnaphthalene, and 2-acetylnaphthalene;

ether compounds such as methoxymethylbenzene, 1-methoxymethyl-2-methylbenzene, 1-methoxymethyl-3-methylbenzene, 1-methoxymethyl-4-methylbenzene, 1-methoxymethyl-2,4-dimethylbenzene, 1-methoxymethyl-2,4,5-trimethylbenzene, 1-dimethoxymethyl-2-methylbenzene, 1-dimethoxymethyl-3-methylbenzene, 1-dimethoxymethyl-4-methylbenzene, and 1-dimethoxymethyl-2,4,5-trimethylbenzene; and ester compounds such as methyl 2-methylbenzoate, methyl 3-methylbenzoate, methyl 4-methylbenzoate, methyl 2,4-dimethylbenzoate, methyl 3,4-dimethylbenzoate, methyl 3,5-dimethylbenzoate, dimethyl 4-methylphthalate, dimethyl 4-methylisophthalate, dimethyl 5-methylisophthalate, dimethyl 2-methylterephthalate, methyl 2,4,5-trimethylbenzoate, dimethyl 4,5-dimethylphthalate, dimethyl 4,6-dimethylisophthalate, dimethyl 2,5-dimethylterephthalate, trimethyl 5-methyltrimellitate, methyl 6-methylnaphthalene-2-carboxylate, methyl 5-methylnaphthalene-1-carboxylate, methyl 4'-methyl-biphenyl-4-carboxylate, phthalide, methyl phthalide, and dimethyl phthalide.

Examples of the aromatic carboxylic acid produced through partial oxidation of the aforementioned aromatic compounds include benzoic acid, phthalic anhydride, isophthalic acid, terephthalic acid, trimellitic anhydride, pyromellitic dianhydride, naphthalenemonocarboxylic acids, naphthalenedicarboxylic acids, naphthalenedicarboxylic anhydride, biphenylmonocarboxylic acids, biphenyldicarboxylic acids, and biphenyldicarboxylic anhydride, In the present invention, among the aforementioned aromatic compounds, when xylene, 1,2,4,5-tetraalkylbenzene having C1 to C3 alkyl groups, and 2,4,5-trialkylbenzaldehyde having C1 to C3 alkyl groups (inter alia 1,2,4,5-tetramethylbenzene and 2,4,5-trimethylbenzaldehyde) are used, particularly excellent performance of the catalyst of the present invention can be attained.

For example, when a mixture of xylene isomers (o-xylene, m-xylene, and p-xylene) is employed as an aromatic compound, aromatic carboxylic acids such as benzoic acid, phthalic anhydride, isophthalic acid, and terephthalic acid can be produced. When 1,2,4,5-tetraalkylbenzene having C1 to C3 alkyl groups or 2,4,5-trialkylbenzaldehyde having C1 to C3 alkyl groups is employed, pyromellitic dianhydride and similar compounds can be produced.

Reaction Conditions, Etc.

No particular limitation is imposed on the reaction mode and reaction conditions of vapor-phase partial oxidation in the production method of the present invention, and known modes and conditions may be employed. The catalyst layer may be designed as a fluidized bed or a fixed bed, and the gas is caused to flow through the catalyst layer.

When the flow manner on a fluidized bed is employed, a fine particulate catalyst which is not supported on a carrier is generally employed. Catalyst properties (particle size, particle size distribution, etc.) and reaction conditions suitable for partial oxidation reaction performed under fluid conditions are selected. When the flow manner on a fixed bed is employed, a shaped catalyst formed of a catalyst which is not supported on a carrier, or a shaped catalyst formed of a catalyst which is supported on a carrier, is generally employed. Catalyst properties (shape, dimensions, etc.) and reaction conditions suitable for partial oxidation reaction performed under immobilized conditions are selected. Also, in the case of the flow manner on a fixed bed, a plurality of catalysts having different catalyst compositions and amounts of catalyst components are generally inserted into a reaction tube in a multi-layer manner. For example, a catalyst layer containing the catalyst of the present invention may be employed as at least one layer or all layers of the multi-layered catalyst. The mode of use of the catalyst may be appropriately selected in consideration of the aforementioned factors. In the present invention, the flow manner on a fixed bed is preferred, since the mode can be adapted under various conditions.

The reaction temperature (temperature of heating medium) is preferably 250 to 550° C., more preferably 300 to 500° C. When the reaction temperature is higher than 250° C., sufficient reaction rate can be attained, whereas when the temperature is lower than 550° C., the yields of partial oxidation products do not decrease, by virtue of suppression of complete combustion. Both cases are preferred. The gas space velocity is 500 to 10,000 $hr^{-1}$, preferably 1,000 to 8,000 $hr^{-1}$. The concentration of material gas (in 1 $m^3$ of oxygen-containing gas (standard state)) is 5 to 200 $g/m^3$, preferably 10 to 100 $g/m^3$. No particular limitation is imposed on the oxygen-containing gas employed in the present invention, so long as the gas contains molecular oxygen. Air, oxygen, and a mixture thereof with an inert gas such as nitrogen, carbon dioxide, helium, or argon at an appropriate ratio may be employed.

In general, vapor-phase partial oxidation of an organic compound by use of an oxygen-containing gas is known to be a vigorously exothermic reaction involving complete combustion. In order to disperse heat of the reaction, in fact, Japanese Patent 1982-105241A and 1986-28456A disclose self-sintered carriers made of high-purity silicon carbide as suitable carriers with high thermal conductivity. However, since such carriers are produced in an inert (non-oxidizing) gas (e.g., nitrogen) atmosphere via a sintering step at very high temperature, the production cost problematically increases. Among silicon carbide carriers, those having a low-purity and containing silica (particularly in a surface portion) is inexpensive and can be produced in a simple manner through calcinating in air at low temperature. However, such a silicon carbide carrier is difficult to exhibit good reaction results.

In a further study conducted by the present inventors on the catalyst of the present invention, the inventors have surprisingly found that a partial oxidation product can be produced at high yield virtually regardless of the purity of silicon carbide of the carrier by virtue of diamond incorporated into the catalyst, even in the reaction system where the yield of a partial oxidation product can be attained with high dependence on the purity of silicon carbide of the carrier when the system employs a catalyst-on-carrier having a catalyst containing an oxide component but no diamond. Therefore, addition of diamond to a partial oxidation catalyst not only enhances the partial oxidation catalytic activity and reaction selectivity, but also enables production of the catalyst from less expensive carrier material instead of particular and expensive carrier material.

EXAMPLES

The present invention will next be described in more detail by way of examples, which should not be construed as limiting the invention thereto.

Catalyst Carriers

The following two commercial shaped catalyst carriers (product of Saint-Gobain N or Pro) were employed. The carriers are mainly formed from silicon carbide.

Carrier (a):
  High-purity silicon carbide carrier produced through calcinating under inert gas
  Shape: Ring-shaped product (outer diam. 7φ×inner diam. 3φ×height 5 mm)
  BET specific surface area: 0.06 $m^2/g$
  Pore volume: 0.29 mL/g
  Porosity: 44.0%

Carrier (b):
  Silicon carbide carrier produced through calcinating in air
  Shape: Ring-shaped product (outer diam. 6φ×inner diam. 3φ×height 6 mm)
  BET specific surface area: 0.05 $m^2/g$
  Pore volume: 0.24 mL/g
  Porosity: 44.3%

Figure 2:
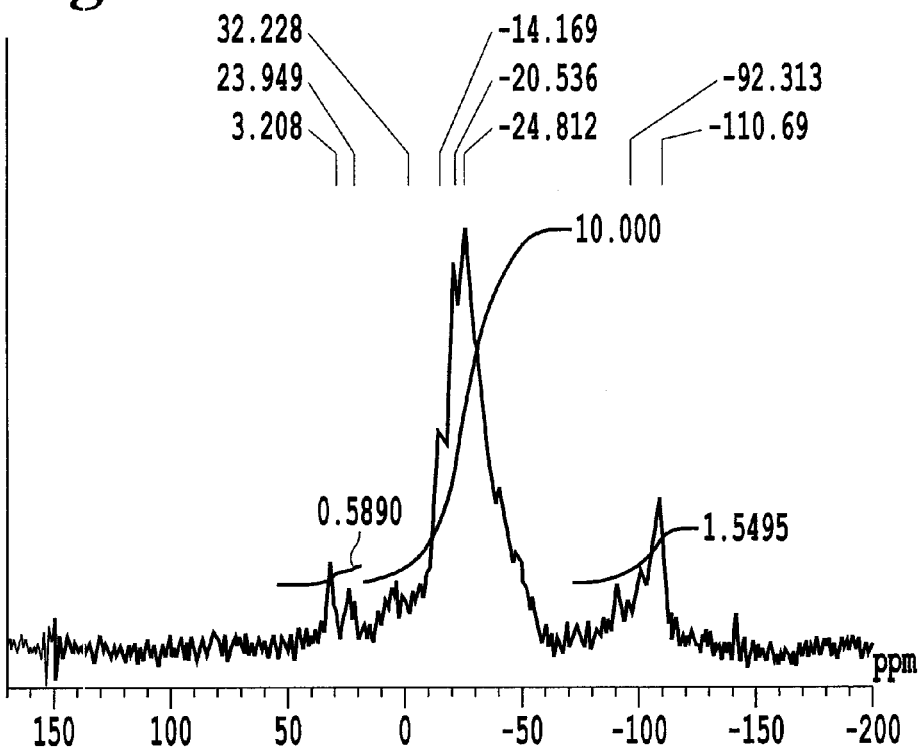
FIG. 2 is a $^{29}$Si MAS-NMR spectrum chart of silicon carbide shaped carrier (b)
Figure 3:
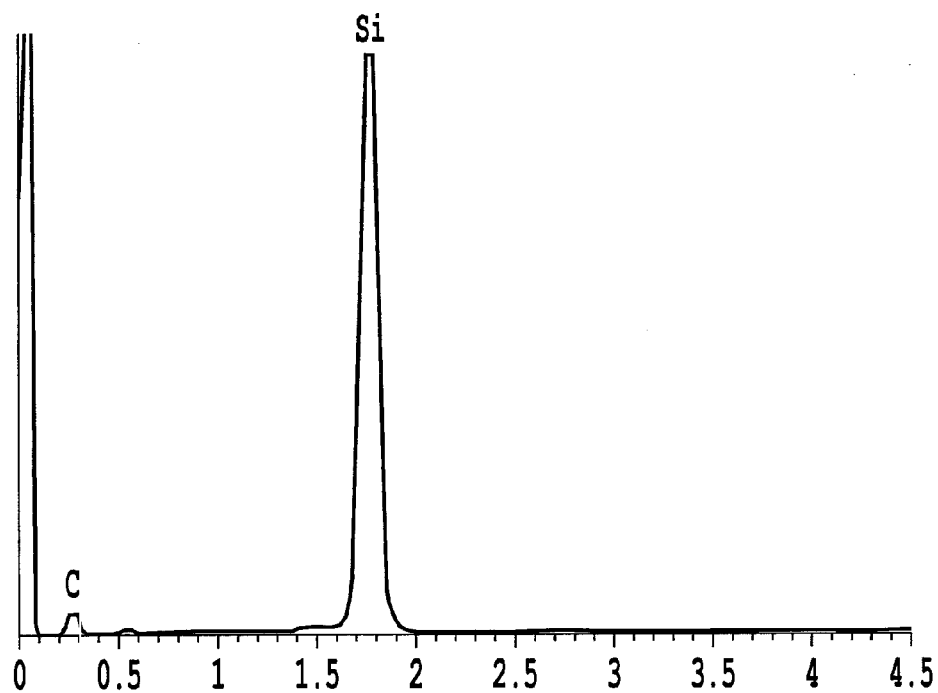
FIG. 3 is a chart showing the results of energy dispersive X-ray analysis of silicon carbide shaped carrier (a)
Figure 4:
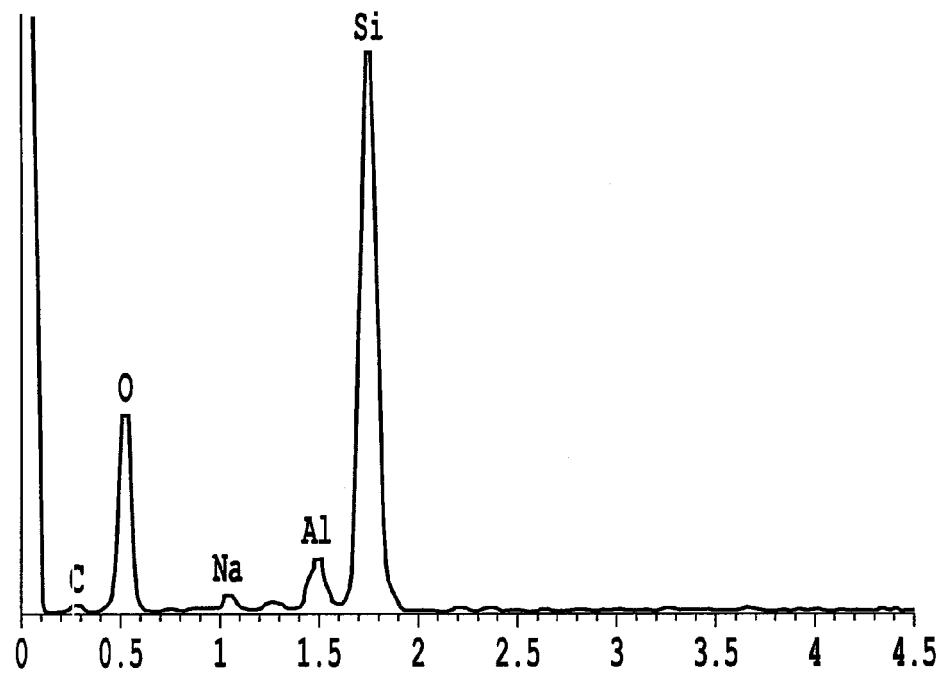
FIG. 4 is a chart showing the results of energy dispersive X-ray analysis of silicon carbide shaped carrier (b).

The two carriers were analyzed through $^{29}$Si MAS-NMR spectrometry. FIGS. 1 and 2 show $^{29}$Si MAS-NMR spectra of carrier (a) and carrier (b), respectively. J. Ceram. Soc. Jpn., 108, p. 1110-1113 (2000) and J. Am. Chem. Soc., 109, p. 6059-67 (1987) describe that a signal having a peak in a range of about −10 to about −30 PPM of a $^{29}$Si MAS-NMR spectrum is assigned to silicon carbide, and a signal having a peak in a range of about −110 to about −120 PPM is assigned to silicon oxide. Therefore, as is clear from FIGS. 1 and 2, carrier (a) shown in FIG. 1 is virtually formed of silicon carbide and contains no silicon oxide. Carrier (b) shown in FIG. 2 contains silicon carbide and silicon oxide. The two carriers were also subjected to surface elemental analysis through SEM-EDX. FIGS. 3 and 4 and Table 1 show the results. Through elemental analysis, the surface of carrier (a) was found to be formed exclusively of carbon and silicon, indicating that carrier (a) was formed of high-purity silicon carbide. In contrast, a large amount of oxygen was detected in carrier (b), and most of the detected metallic elements were silicon, indicating that carrier (b) has a large amount of silicon oxide in the surface thereof.

$^{29}$Si MAS-NMR analysis conditions
Apparatus: JNM-EX270 Solid NMR system (JEOL)
Mode of measurement: MASGNN (Magic Angle Spin without decoupling)
Temperature of measurement: room temperature (22° C.)
Pulse width (PW1): 4.5 μs
Dead Time: 27.8 μs
Repeating time (PD): 15 s SEM-EDX analysis conditions
Apparatus: SEM (S-3400N, Hitachi High-technology); EDX (energy dispersive X-ray) analyzer (EX-350, Horiba Seisaku-sho)
Mode of measurement: low vacuum mode, 30 Pa, acceleration voltage 15 kV, WD 10 mm, reflected electron detector

TABLE 1

| Elements | Carrier (a) atomic concentration (%) | Carrier (b) atomic concentration (%) |
|---|---|---|
| C (K-ray) | 53.31 | 10.85 |
| O (K-ray) | 0.00 | 55.45 |
| Na (K-ray) | 0.00 | 0.89 |
| Al (K-ray) | 0.00 | 2.53 |
| Si (K-ray) | 46.69 | 30.28 |
| Total | 100.00 | 100.00 |

Example 1

Ammonium vanadate [$NH_4VO_3$] (1.81 g) (commercial reagent, product of Wako Pure Chemical Industries, Ltd.), ammonium titanyl oxalate [$(NH_4)_2TiO(C_2O_4)_2$] (2.56 g), and oxalic acid [$(COOH)_2$] (2.74 g) (product of Soekawa Chemical Co., Ltd.) were dissolved in ion-exchange water (100 mL) at 50° C., to thereby prepare a material solution. To the solution, anatase titanium dioxide powder (commercial product, BET specific surface area: 28.0 m$^2$/g, pore volume: 0.17 mL/g) (10.5 g) and natural diamond powder (commercial product, particle size: 0 to 1 μm grade, BET specific surface area: 24.9 m$^2$/g, pore volume: 0.23 mL/g) (1.0 g) were added with sufficient mixing, to thereby prepare a slurry. The aforementioned silicon carbide carrier (a) was heated at 150° C. or higher, and the slurry was sprayed to the carrier while heating of the carrier was continued, to thereby cause the catalyst components to be impregnated on the carrier. Subsequently, the formed catalyst-on-carrier was calcinated in an electric furnace at 500° C. for 3 hours, to thereby produce a catalyst product. The amount of catalyst impregnated by the carrier and the composition of the catalyst are shown in Table 2-1.

The thus-produced catalyst (7.5 g) was charged into a tube reactor (inner diam.: 18 mm, length: 500 mm), and the reactor was immersed in a molten salt (potassium nitrate and sodium nitrate) bath. The temperature of the molten salt bath was adjusted (see Table 3), and a gas of 2,4,5-trimethylbenzaldehyde (12.3 g/Nm$^3$-air) was caused to pass through the reactor under normal pressure at a specific gas space velocity (see Table 3), to thereby perform catalytic oxidation reaction. The reaction products were analyzed through gas chromatography. The yield of formed pyromellitic dianhydride was calculated with respect to the amount by mole of 2,4,5-trimethylbenzaldehyde fed to the reactor. The results along with the molten salt bath temperature and space velocity are shown in Table 3-1.

Comparative Example 1

The procedure of Example 1 was repeated, except that a slurry was prepared without using diamond, to thereby produce a catalyst. The composition of the catalyst and the amount of catalyst impregnated by the carrier are shown in Table 2-1. In a manner similar to that of Example 1, catalytic oxidation of 2,4,5-trimethylbenzaldehyde was carried out. The results along with the molten salt bath temperature and space velocity are shown in Table 3-1.

Example 2

The procedure of Example 1 was repeated, except that a material solution was prepared through further addition of ammonium paramolybdate [$(NH_4)_6Mo_7O_{24}$] (0.95 g), to thereby produce a catalyst. The composition of the catalyst and the amount of catalyst impregnated by the carrier are shown in Table 2-2. In a manner similar to that of Example 1, catalytic oxidation of 2,4,5-trimethylbenzaldehyde was carried out. The results along with the molten salt bath temperature and space velocity are shown in Table 3-2.

Comparative Example 2

The procedure of Example 2 was repeated, except that a slurry was prepared without using diamond, to thereby produce a catalyst. The composition of the catalyst and the amount of catalyst impregnated by the carrier are shown in Table 2-2. In a manner similar to that of Example 1, catalytic oxidation of 2,4,5-trimethylbenzaldehyde was carried out. The results along with the molten salt bath temperature and space velocity are shown in Table 3-2.

Example 3

The procedure of Example 1 was repeated, except that a material solution was prepared through further addition of ammonium dihydrogenphosphate [$NH_4H_2PO_4$] (0.62 g), to thereby produce a catalyst. The composition of the catalyst and the amount of catalyst impregnated by the carrier are shown in Table 2-2. In a manner similar to that of Example 1, catalytic oxidation of 2,4,5-trimethylbenzaldehyde was carried out. The results along with the molten salt bath temperature and space velocity are shown in Table 3-2.

Comparative Example 3

The procedure of Example 3 was repeated, except that a slurry was prepared without using diamond, to thereby produce a catalyst. The composition of the catalyst and the amount of catalyst impregnated by the carrier are shown in Table 2-2. In a manner similar to that of Example 1, catalytic oxidation of 2,4,5-trimethylbenzaldehyde was carried out. The results along with the molten salt bath temperature and space velocity are shown in Table 3-2.

Example 4

The procedure of Example 3 was repeated, except that the natural diamond powder was changed to synthetic diamond powder (commercial product, mean particle size $d_{50}$: 0.208 μm, particle size $d_{10}$: 0.128 μm, particle size $d_{90}$: 0.307 μm,

TABLE 2-1

| Catalyst | Carrier | Diamond | Amount (wt. %) | Composition (wt. %) | | | | | | |
| --- | --- | --- | --- | --- | --- | --- | --- | --- | --- | --- |
| | | | | $V_2O_5$ | $TiO_2$ | $MoO_3$ | $P_2O_5$ | $B_2O_3$ | diamond | SiC |
| Ex. 1 | (a) | natural | 4.0 | 0.45 | 3.3 | — | — | — | 0.27 | — |
| Comp. Ex. 1 | (a) | — | 3.8 | 0.46 | 3.3 | — | — | — | — | — |

TABLE 3-1

| Catalyst | Space velocity (hr$^{-1}$) | Molten salt bath temp. (° C.) | Pyromellitic dianhydride yield (%) |
| --- | --- | --- | --- |
| Ex. 1 | 2,840 | 365° C. | 52.6 |
| Comp. Ex. 1 | 2,840 | 365° C. | 48.1 |

BET specific surface area: 21.2 m²/g, pore volume: 0.18 mL/g) (1.0 g), to thereby produce a catalyst. The composition of the catalyst and the amount of catalyst impregnated by the carrier are shown in Table 2-2. In a manner similar to that of Example 1, catalytic oxidation of 2,4,5-trimethylbenzaldehyde was carried out. The results along with the molten salt bath temperature and space velocity are shown in Table 3-2.

Comparative Example 4

The procedure of Example 3 was repeated, except that a slurry was prepared from silicon carbide powder (commercial product, mean particle size: 0.6 μm, BET specific surface area: 12.4 m²/g, pore volume: 0.16 mL/g) (1.0 g) instead of diamond to thereby produce a catalyst. The composition of the catalyst and the amount of catalyst impregnated by the carrier are shown in Table 2-2. In a manner similar to that of Example 1, catalytic oxidation of 2,4,5-trimethylbenzaldehyde was carried out. The results along with the molten salt bath temperature and space velocity are shown in Table 3-2.

Example 5

The procedure of Example 1 was repeated, except that a material solution was prepared through further addition of ammonium dihydrogenphosphate [$NH_4H_2PO_4$] (0.62 g) and boric acid [$H_3BO_3$] (0.11 g), to thereby produce a catalyst. The composition of the catalyst and the amount of catalyst impregnated by the carrier are shown in Table 2-2. In a manner similar to that of Example 1, catalytic oxidation of 2,4,5-trimethylbenzaldehyde was carried out. The results along with the molten salt bath temperature and space velocity are shown in Table 3-2.

Comparative Example 5

The procedure of Example 5 was repeated, except that a slurry was prepared without using diamond, to thereby produce a catalyst. The composition of the catalyst and the amount of catalyst impregnated by the carrier are shown in Table 2-2. In a manner similar to that of Example 1, catalytic oxidation of 2,4,5-trimethylbenzaldehyde was carried out. The results along with the molten salt bath temperature and space velocity are shown in Table 3-2.

Example 6

The procedure of Example 3 was repeated, except that silicon carbide carrier (a) was changed to carrier (b), to thereby prepare a catalyst. The composition of the catalyst and the amount of catalyst impregnated by the carrier are shown in Table 2-2. In a manner similar to that of Example 1, catalytic oxidation of 2,4,5-trimethylbenzaldehyde was carried out. The results along with the molten salt bath temperature and space velocity are shown in Table 3-2.

Comparative Example 6

The procedure of Example 6 was repeated, except that a slurry was prepared without using diamond, to thereby produce a catalyst. The composition of the catalyst and the amount of catalyst impregnated by the carrier are shown in Table 2-2. In a manner similar to that of Example 1, catalytic oxidation of 2,4,5-trimethylbenzaldehyde was carried out. The results along with the molten salt bath temperature and space velocity are shown in Table 3-2.

TABLE 2-2

| Catalyst | Carrier | Diamond | Amount (wt. %) | $V_2O_5$ | $TiO_2$ | $MoO_3$ | $P_2O_5$ | $B_2O_3$ | diamond | SiC |
|---|---|---|---|---|---|---|---|---|---|---|
| Ex. 2 | (a) | natural | 4.4 | 0.47 | 3.4 | 0.20 | — | — | 0.29 | — |
| Ex. 3 | (a) | natural | 5.7 | 0.63 | 4.6 | — | 0.10 | — | 0.38 | — |
| Ex. 4 | (a) | synthetic | 5.0 | 0.55 | 4.0 | — | 0.09 | — | 0.34 | — |
| Ex. 5 | (a) | natural | 5.5 | 0.60 | 4.4 | — | 0.09 | 0.02 | 0.37 | — |
| Ex. 6 | (b) | natural | 5.8 | 0.64 | 4.7 | — | 0.10 | — | 0.39 | — |
| Comp. Ex. 2 | (a) | — | 4.1 | 0.47 | 3.4 | 0.20 | — | — | — | — |
| Comp. Ex. 3 | (a) | — | 5.2 | 0.62 | 4.5 | — | 0.10 | — | — | — |
| Comp. Ex. 4 | (a) | — | 5.7 | 0.62 | 4.5 | — | 0.10 | — | — | 0.44 |
| Comp. Ex. 5 | (a) | — | 5.3 | 0.62 | 4.6 | — | 0.10 | 0.02 | — | — |
| Comp. Ex. 6 | (b) | — | 5.5 | 0.65 | 4.7 | — | 0.10 | — | — | — |

TABLE 3-2

| Catalyst | Space velocity (hr⁻¹) | Molten salt bath temp. (° C.) | Pyromellitic dianhydride yield (%) |
|---|---|---|---|
| Ex. 2 | 2,840 | 370° C. | 72.6 |
| Ex. 3 | 2,910 | 380° C. | 76.6 |
| Ex. 4 | 2,910 | 385° C. | 72.3 |
| Ex. 5 | 2,780 | 380° C. | 75.0 |
| Ex. 6 | 2,780 | 380° C. | 75.6 |
| Comp. Ex. 2 | 2,840 | 370° C. | 63.2 |
| Comp. Ex. 3 | 2,910 | 380° C. | 67.3 |
| Comp. Ex. 4 | 2,910 | 380° C. | 68.3 |
| Comp. Ex. 5 | 2,780 | 380° C. | 68.3 |
| Comp. Ex. 6 | 2,780 | 380° C. | 59.5 |

Example 7

The procedure of Example 1 was repeated, except that the catalyst prepared in Example 3 was used, and a gas of 1,2,4,5-tetramethylbenzene (10.7 g/Nm³-air) was supplied, to thereby perform catalytic oxidation of 1,2,4,5-tetramethylbenzene. The results along with the molten salt bath temperature and space velocity are shown in Table 4.

Comparative Example 7

The procedure of Example 7 was repeated, except that the catalyst prepared in Comparative Example 3 was used, to thereby perform catalytic oxidation of 1,2,4,5-tetramethylbenzene. The results along with the molten salt bath temperature and space velocity are shown in Table 4.

TABLE 4

| Catalyst | Space velocity (hr$^{-1}$) | Molten salt bath temp. (° C.) | Pyromellitic dianhydride yield (%) |
|---|---|---|---|
| Ex. 7 | 2,840 | 370° C. | 65.3 |
| Comp. Ex. 7 | 2,840 | 370° C. | 53.0 |

According to the present invention, there can be provided a catalyst exhibiting excellent performance particularly in partial oxidation reaction, and a method for efficiently producing carboxylic acid or carboxylic anhydride through vapor-phase partial oxidation of an organic compound by use of an oxygen-containing gas in the presence of the catalyst.

What is claimed is:
1. A catalyst comprising:
   (1) diamond;
   (2) at least one oxide A selected from the group consisting of Group 5 transition element oxides; and
   (3) at least one oxide B selected from the group consisting of Group 4 transition element oxides.
2. The catalyst of claim 1, further comprising:
   (4) at least one oxide C selected from the group consisting of Group 6 transition element oxides.
3. The catalyst of claim 1, further comprising:
   (5) at least one oxide D selected from the group consisting of oxides of elements of Groups 1, 13, 14, 15, and 16, except carbon.
4. The catalyst of claim 1, wherein the oxide A is vanadium oxide, and the oxide B is titanium oxide.
5. The catalyst of claim 2, wherein the oxide A is vanadium oxide, the oxide B is titanium oxide, and the oxide C is at least one selected from the group consisting of molybdenum oxide and chromium oxide.
6. The catalyst of claim 3, wherein the oxide D is at least one selected from the group consisting of oxides of boron, aluminum, germanium, phosphorus, antimony, and tellurium.
7. The catalyst of claim 3, wherein the oxide D is at least one selected from the group consisting of oxides of boron and phosphorus.
8. The catalyst of claim 1, wherein a diamond content is 0.1 to 200 parts by weight with respect to the total amount of oxides A and B of 100 parts by weight.
9. The catalyst of claim 1, which is vapor-phase partial oxidation of an organic compound with an oxygen-containing gas.
10. A catalyst-on-carrier, comprising a carrier and the catalyst of claim 1 supported by the carrier.
11. The catalyst-on-carrier of claim 10, wherein the carrier is a shaped carrier comprising at least one selected from the group consisting of silicon carbide, alumina, silica, zirconia, steatite, cordierite, mullite, porcelain, and a ceramic.
12. The catalyst-on-carrier of claim 10, wherein an amount of catalyst supported by the carrier is 0.1 to 20 wt. % with respect to the weight of the catalyst-on-carrier.
13. A method for producing a carboxylic acid or a carboxylic anhydride, the method comprising oxidizing an organic compound by vapor phase partial oxidation with an oxygen-containing gas in the presence of the catalyst of any one of claims 1 to 8 or the catalyst-on-carrier of any one of claims 10 to 12, wherein the organic compound is an aromatic compound having one or more substituents in a molecule thereof, the substituents each including a carbon atom bonded to an aromatic ring.
14. The production method of claim 13, wherein the one or more substituents are at least one selected from the group consisting of a methyl group, an ethyl group, a propyl group, an acetyl group, and a formyl group.
15. The production method of claim 13, wherein the aromatic compound is at least one selected from the group consisting of o-xylene, m-xylene, and p-xylene.
16. The production method of claim 13, wherein the aromatic compound is 1,2,4,5-tetraalkylbenzene, 2,4,5-trialkylbenzaldehyde, or both.
17. The production method of claim 13, wherein the aromatic compound is 1,2,4,5-tetramethylbenzene, 2,4,5-trimethylbenzaldehyde, or both.
18. The production method of claim 13, wherein the vapor-phase partial oxidation occurs in a flow manner on a fixed bed.

\* \* \* \* \*